(12) United States Patent
Heino et al.

(10) Patent No.: US 9,855,084 B2
(45) Date of Patent: Jan. 2, 2018

(54) BIOABSORBABLE, ORIENTED, DEFORMABLE FIXATION MATERIAL AND PLATE

(75) Inventors: Harri Heino, Tampere (FI); Pertti Törmälä, Tampere (FI); Kalle Räsänen, Nokia (FI); Jarkko Haarjärvi, Tampere (FI)

(73) Assignee: BIORETEC OY, Tampere (FI)

( * ) Notice: Subject to any disclaimer, the term of this patent is extended or adjusted under 35 U.S.C. 154(b) by 891 days.

(21) Appl. No.: 14/240,183

(22) PCT Filed: Aug. 27, 2012

(86) PCT No.: PCT/FI2012/050812
§ 371 (c)(1),
(2), (4) Date: Sep. 25, 2014

(87) PCT Pub. No.: WO2013/030446
PCT Pub. Date: Mar. 7, 2013

(65) Prior Publication Data
US 2015/0032167 A1    Jan. 29, 2015

(30) Foreign Application Priority Data
Aug. 26, 2011 (FI) ..................................... 20115834

(51) Int. Cl.
*A61B 17/80* (2006.01)
*B29C 55/10* (2006.01)
(Continued)

(52) U.S. Cl.
CPC ........ *A61B 17/8085* (2013.01); *A61B 17/688* (2013.01); *A61B 17/7059* (2013.01);
(Continued)

(58) Field of Classification Search
CPC . A61B 17/80; A61B 17/8033; A61B 17/8038; A61B 17/8042; A61B 17/8047;
(Continued)

(56) References Cited

U.S. PATENT DOCUMENTS

| 4,403,606 A | * | 9/1983 | Woo | A61B 17/80 606/70 |
| 4,403,607 A | * | 9/1983 | Woo | A61B 17/80 606/70 |

(Continued)

FOREIGN PATENT DOCUMENTS

| EP | 0146398 A2 | 6/1985 |
| EP | 0 449 867 B1 | 4/1994 |

(Continued)

OTHER PUBLICATIONS

European Paten Office Extended European Search Report dated Dec. 3, 2015 for EP application No. 12828168.0.
(Continued)

*Primary Examiner* — Christian Sevilla
*Assistant Examiner* — Eric S Gibson
(74) *Attorney, Agent, or Firm* — Berggren Inc.

(57) ABSTRACT

A bioabsorbable surgical osteosynthesis plate operable to be secured by at least one fastener through at least one fastener opening formed in the plate to a bone. The plate includes a flat section having first and second surfaces defining a main plane of the plate. The plate includes a polymer material that is oriented multiaxially and is substantially rigid and substantially deformable at a first thermochemical state. In the multiaxially oriented structure of the plate the polymer material is arranged according to at least three different orientation axes along the main plane of the plate as a result of solid state drawing of the plate. The polymer material of
(Continued)

the plate has isotropic mechanical tear properties in different directions along the main plane of the plate.

12 Claims, 7 Drawing Sheets

(51) Int. Cl.
| | |
|---|---|
| A61L 31/06 | (2006.01) |
| A61L 31/14 | (2006.01) |
| A61L 31/12 | (2006.01) |
| A61B 17/70 | (2006.01) |
| A61B 17/68 | (2006.01) |
| B29B 11/10 | (2006.01) |
| B29C 55/16 | (2006.01) |
| A61B 17/00 | (2006.01) |

(52) U.S. Cl.
CPC .......... *A61B 17/80* (2013.01); *A61B 17/8061* (2013.01); *A61L 31/06* (2013.01); *A61L 31/128* (2013.01); *A61L 31/14* (2013.01); *A61L 31/148* (2013.01); *B29B 11/10* (2013.01); *B29C 55/10* (2013.01); *B29C 55/16* (2013.01); *A61B 2017/00004* (2013.01); *A61L 2430/02* (2013.01); *B29K 2995/006* (2013.01); *B29K 2995/0056* (2013.01)

(58) Field of Classification Search
CPC ............ A61B 17/8052; A61B 17/8057; A61B 17/8061–17/8076; A61B 17/8085; A61B 17/809; B29C 55/10; B29C 55/12; B29C 55/14; B29C 55/143; B29C 55/146; B29C 55/16; B29C 55/165
USPC ..................................... 606/70, 71, 280–299
See application file for complete search history.

(56) References Cited

U.S. PATENT DOCUMENTS

| | | | | |
|---|---|---|---|---|
| 4,671,280 | A * | 6/1987 | Dorband | A61B 17/0643 264/328.11 |
| 4,898,186 | A | 2/1990 | Ikada et al. | |
| 4,968,317 | A * | 11/1990 | Tormala | A61B 17/80 606/76 |
| 5,023,120 | A * | 6/1991 | Akao | B29C 55/023 428/216 |
| 5,030,402 | A * | 7/1991 | Zachariades | A61F 2/30 264/138 |
| 5,541,011 | A * | 7/1996 | Takashige | B29C 55/12 428/213 |
| 5,569,250 | A * | 10/1996 | Sarver | A61B 17/688 606/281 |
| 5,641,566 | A | 6/1997 | Kranzler et al. | |
| 6,048,480 | A * | 4/2000 | Doyle | A61L 27/16 264/138 |
| 6,099,791 | A * | 8/2000 | Shannon | B29C 55/045 264/127 |
| 6,221,075 | B1 * | 4/2001 | Tormala | A61B 17/80 606/283 |
| 6,406,498 | B1 * | 6/2002 | Tormala | A61L 27/446 623/11.11 |
| 6,632,503 | B1 * | 10/2003 | Shikinami | A61B 17/8085 428/131 |
| 6,692,497 | B1 | 2/2004 | Tormala et al. | |
| 6,692,498 | B1 * | 2/2004 | Niiranen | A61B 17/80 606/70 |
| 8,414,654 | B1 * | 4/2013 | Ganey | A61F 2/28 623/16.11 |
| 2003/0206928 | A1 * | 11/2003 | Tormala | A61L 31/128 424/400 |
| 2005/0107529 | A1 * | 5/2005 | Datta | C08F 210/18 525/70 |
| 2005/0261780 | A1 * | 11/2005 | Heino | A61B 17/8085 623/23.51 |
| 2006/0183860 | A1 * | 8/2006 | Mehta | C08L 23/10 525/191 |
| 2006/0275734 | A1 | 12/2006 | Vallittu et al. | |
| 2007/0132155 | A1 * | 6/2007 | Burgermeister | A61L 31/04 264/479 |
| 2007/0270852 | A1 * | 11/2007 | Tormala | A61B 17/80 606/281 |
| 2008/0071299 | A1 * | 3/2008 | Allinniemi | A61B 17/68 606/151 |
| 2008/0083999 | A1 * | 4/2008 | Merrill | B29C 55/146 264/2.7 |
| 2008/0111277 | A1 * | 5/2008 | Nichols | B29C 55/30 264/292 |
| 2009/0053959 | A1 * | 2/2009 | Datta | B32B 5/26 442/328 |
| 2009/0155534 | A1 * | 6/2009 | O'Brien | B29C 47/0014 428/156 |
| 2009/0283701 | A1 * | 11/2009 | Ogawa | A61B 17/866 250/492.1 |
| 2010/0190920 | A1 * | 7/2010 | Bellare | B29C 55/005 524/585 |
| 2010/0191292 | A1 * | 7/2010 | DeMeo | A61B 17/80 606/301 |
| 2010/0227144 | A1 * | 9/2010 | Nichols | B29C 55/005 428/220 |
| 2010/0245730 | A1 * | 9/2010 | Nimura | B29C 55/14 349/96 |
| 2010/0292374 | A1 * | 11/2010 | Bellare | B29C 47/0016 524/110 |
| 2011/0027568 | A1 * | 2/2011 | Nihlstrand | C09K 5/063 428/221 |
| 2011/0189472 | A1 * | 8/2011 | Roberts | B01D 67/0004 428/323 |
| 2011/0236702 | A1 * | 9/2011 | Busch | B29B 17/0005 428/461 |
| 2011/0319585 | A1 * | 12/2011 | Uehara | B29C 55/16 526/352 |
| 2015/0032167 | A1 * | 1/2015 | Heino | B29B 11/08 606/284 |
| 2016/0183990 | A1 * | 6/2016 | Koizumi | C12M 25/02 606/285 |

FOREIGN PATENT DOCUMENTS

| | | |
|---|---|---|
| EP | 0321 176 B1 | 2/1995 |
| EP | 0987033 B1 | 6/2003 |
| FI | 88111 | 10/1990 |
| FI | 101933 B | 12/1996 |
| FI | 98136 B | 1/1997 |
| FI | 955547 | 5/1997 |
| GB | 2307179 A | 5/1997 |
| WO | WO-90/04982 A1 | 5/1990 |
| WO | WO-90/07304 A1 | 7/1990 |
| WO | WO-90/12550 A1 | 11/1990 |
| WO | WO-96/41596 A1 | 12/1996 |
| WO | WO-97/11725 A1 | 4/1997 |
| WO | 01/62136 A2 | 8/2001 |

OTHER PUBLICATIONS

Journal of Biomedical Materials Research, vol. 29, No. 11, Nov. 1995; J. M. Anderson, "Journal of Biomedical Materials Research";
S.I. Ertel et al., "Evaluation of poly(DTH carbonate), a tyrosine-derived degradable polymer, for orthopedic application"; Journal of Biomedical Materials Research, vol. 29, pp. 1337-1348, 1995.
K. Bessho et al., "A Bioabsorbable Poly-L-Lactide Miniplace and Screw System for Osteosynthesis in Oral and Maxillofacial Surgery", American Association of Oral and Maxillofacial Surgeons, 1997, pp. 941-945.

(56) References Cited

OTHER PUBLICATIONS

S. Vainionpaa et al; Progress in Polymer Science; Surgical Applications of Biodegradable Polymers in Human Tissues; vol. 14, 1989, pp. 679-719.
D.C. Tunc et al.; Development of Absorbable, Ultra High Strength Poly(Lactides); Progress in Biomedical Polymers; pp. 239-248.
J. Eitenmuller et al.; European Congress on Biomaterials; An In Vivo Evaluation of a New High Molecular Weight Polylactide Osteosynthesis Device.

* cited by examiner

BIOABSORBABLE, ORIENTED, DEFORMABLE FIXATION MATERIAL AND PLATE

CROSS-REFERENCE TO RELATED APPLICATIONS

This application claims priority to Finnish patent application 20115834 filed 26 Aug. 2011 and is the national phase of PCT/FI2012/050812 filed 27 Aug. 2012.

FIELD OF THE INVENTION

The present invention relates to surgical materials and implants, methods to manufacture such materials and implants and a method to use such materials and implants and, more particularly, to bodily tissue fixation systems including bodily tissue fixation implants comprising bioabsorbable polymeric and/or composite plates.

BACKGROUND OF THE INVENTION

Because of shortcomings of metallic plates, bioabsorbable, polymeric plates have been developed for fracture fixation in bone surgery. E.g. elongated, bioabsorbable, six-hole plates were developed by Eitenmüller et al. for orthopaedic animal studies (European Congress on Biomaterials, Abstracts, Instituto Rizzoli, Bologna, 1986, p. 94). However, because of inadequate strength, some of the fracture fixation plates were broken in animal experiments.

U.S. Pat. No. 5,569,250 describes a biocompatible osteosynthesis plate operable for being enhanced in a substantially secured relation to a plurality of adjacent bone portions. The osteosynthesis plate is in a first configuration at a first thermochemical state and is operable to be converted to a second thermochemical state so that it may be deformed prior to fixation.

The first thermochemical state is typically room temperature (operation room conditions) and the second thermochemical state is typically an elevated temperature above $T_g$ of the polymer material (e.g. for polylactides between 50-60° C.). Accordingly, the plates of U.S. Pat. No. 5,569,250 must be changed from the first thermochemical state to the second thermochemical state, to be shaped (deformed) and thereafter they must be changed again back to the first thermochemical state prior to fixation. Because the thermal conductivity of polymeric materials is poor, the conversion of material to a second temperature is a slow process. Therefore, the clinical use of plates of U.S. Pat. No. 5,569,250 is tedious, slow and complex especially if the surgeon must shape the plate several times to make it fit exactly to the form of the bone to be fixed.

K. Bessho et al., J. Oral. Maxillofac. Surg. 55 (1997) 941-945, describe bioabsorbable poly-L-lactide miniplate and screw system for osteosynthesis in oral and maxillofacial surgery. Also these plates must be heated by immersion in a hot sterilized physiologic salt solution or by the application of hot air until they become plastic and can only then be fitted to the surface of the bone.

EP 0 449 867 B1 describes a plate for fixation of a bone fracture, osteotomy, arthrodesis etc. said plate being intended to be fixed on bone at least with one fixation device, like screw, rod, clamp or corresponding, wherein the plate comprises at least two essentially superimposed plates, so as to provide a multilayer plate construction, so that the individual plates of said multilayer plate construction are flexible so as to provide a change of form of said multilayer plate construction to substantially assume the shape of the bone surface in the operation conditions by means of an external force such as by hand and/or by bending instrument directed to said multilayer plate construction, whereby each individual plate assumes the position of its own with respect to other individual plates by differential motion along the coinciding surfaces.

Although the said multilayer plate fits even the curved bone surface without heating of individual plates, the clinical use of multilayer plate is tedious, because the single plates easily slip in relation to each other before fixation. Additionally the thickness of multilayer plate system easily becomes too thick for cranio maxillofacial applications, causing cosmetic disturbance and increased risks for foreign body reaction.

EP 0 987 033 A1 corresponding to U.S. Pat. No. 6,632,503 describes a biodegradable and bioabsorbable implant material wherein its shape after deformation within ordinary temperature range can be fixed and maintained so that its shape can be easily adjusted at the site of operation, and it has substantially no anisotropy in view of strength. Particularly, it provides an implant material which can effect deformation such as bending or twisting within ordinary temperature range and has a shape-keeping ability to fix and maintain the shape after deformation as such, wherein molecular chains, domains of molecular chain assembly or crystals of the polymer are oriented along a large number of reference axes having random axial directions.

In manufacturing the implant material, an injection molded or extrusion molded billet is first pressed at low temperature to a bottom-closed forming mold having smaller dimensions that the billet, to prepare a forged molding block (first forging step), and the forged molding block, as such or after cutting into an appropriate size, is then forged a second time in a mechanical direction that is different from the direction of pressing in the first forging step. According the document, in the second time forging the crystals of the polymer, which have been oriented in parallel along many reference axes in the first forging step, are subjected to rearrangement in the mechanical direction so that the many reference axes direct toward various directions randomly. As a result, the crystals of the polymer are oriented along a large number of reference axes having different axial directions, or clusters having these reference axes having different orientation are assembled in a large number. The small orientation units of molecular chains, domains of molecular chain assembly or crystals of EP 0 987 033 A1, form a non-continuous, random (non-directed) reinforcement into the material, analogous with the random short-fiber or whisker reinforcement. However, it should be advantageous to have in the oriented plate material a multiaxial continuous orientation, while long, continuous orientation units give usually better mechanical property combination for the material than short ones.

Random axial directions of small orientation units of molecular chains, domains of molecular chain assembly or crystals could make the material structure unfavorable to resist tear (plate cutting) loads between holes with fixation screws, which tear loads originate from the tendency of bone fragments to draw apart in relation to each others (typically in the plane of the flat surface and long axis of the plate).

Even if the implant material of EP 0 987 033 A1 can be bended or twisted within ordinary temperature range, it is manufactured with a complex non-continuous process including first melt molding and thereafter secondly and thirdly, or even more non-continuous forging (solid state molding) steps.

U.S. Pat. No. 6,221,075 and U.S. Pat. No. 6,692,497 describe bioabsorbable osteosynthesis plate and its surgical use. The plate is made of a material that is oriented uni- and/or biaxially and is substantially rigid and deformable at temperatures below the glass transition temperature of the material.

Uniaxially oriented plate material has good mechanical strength in the tensile mode, in the direction of orientation but it is strongly anisotropic so that longitudinal splitting of the material is a risk, when multiaxial mechanical forces are stressing the plate. Also biaxial orientation yields materials with anisotropic mechanical properties, because orientation structure is not uniform in different directions.

US Pat. Appl. published as US 2007/270852 A describes a bioabsorbable surgical osteosynthesis plate that is substantially rigid and deformable at temperatures below the glass transition temperature ($T_g$) of the material, that plate having multiaxial spiral orientation.

The multiaxial spiral orientation is received by turning the ends of an elongated, solid preform (billet) to opposite directions so that the preform twists itself along its long axis. When compressing the spiral oriented preform to a plate-like billet at a temperature above the glass transition temperature, $T_g$, of the material but below its melting temperature, $T_m$ (if any), a multiaxial spiral oriented plate preform is obtained. Even if the spiral oriented, multiaxially oriented plate has not some of the limitations of uni- or biaxially oriented plates, it is impossible to manufacture broad plates, like mesh-plates with this method, due to the delamination of material layers inside of the plate structure caused by shear forces developed in the compression molding of the material to form a plate out of the cylindrical preform. Delamination of the material can be seen as fracture surfaces inside of the plate, parallel with the broad surfaces of the plate.

Therefore, there is a need of bioabsorbable (bioresorbable or biodegradable) oriented material or plate, which:
- can be deformed, yet is dimensionally stable at temperatures below $T_g$ of the material
- has more isotropic mechanical properties than uni- and biaxially oriented materials have
- does not possess the tendency to internal delamination
- can be made also in the form of broad mesh-plates.

A need also exists for a bioabsorbable (bioresorbable or biodegradable) broad osteosynthesis material and plate, which is strong and tough, does not produce a substantial inflammatory response, which has isotropic tear load carrying capacity in different directions of the plate surface and has a good resistance against longitudinal splitting and against internal delamination and which material or plate can be deformed, yet is dimensionally stable at temperatures below $T_g$ of the material from which the device is made, to facilitate shaping.

A need also exists for such a bioabsorbable (bioresorbable or biodegradable) osteosynthesis material and plate, which is broad, strong, tough, does not produce a substantial inflammatory response, which has an isotropic resistance against splitting and against internal delamination which material or plate can be deformed, yet is dimensionally stable, in operation room conditions, to facilitate the shaping of the plate.

A need also exists for such a material and plate, which is thin (the thickness typically from 0.1 mm up to 6 mm), long and broad, so that it can be used as or formed to a mesh plate with the length (l) and the width (w) of several centimeters (e.g. l=10 cm, w=10 cm).

A need also exists for such a material and plate, which has the length and the width of several centimeters, so that the material can be cut advantageously with mechanical and/or thermomechanical methods to smaller osteosynthesis plates.

A need also exists for such a bioabsorbable (bioresorbable or biodegradable) osteosynthesis material and plate, which is strong, tough, does not produce a substantial inflammatory response, which has an isotropic resistance against splitting in all directions of the surface plane and against internal delamination and which material and plate can be deformed, yet is dimensionally stable in operation room conditions (in the first thermochemical state) to allow its fixation on bone without distortion of the configuration of the bone fragments to be fixed, and which shaped plate is also dimensionally stable in tissue conditions (in the second thermochemical state), when fixed on bone surface to facilitate non-problematic healing of bone fracture.

A need also exists for such a bioabsorbable osteosynthesis plate preform, which has a good resistance against splitting (tear) in different directions of the surface plane and which plate preform can be processed economically (rapidly and effectively) to smaller plates e.g. with mechanical cutting or laser cutting, giving smaller plates with isotropic mechanical properties.

SUMMARY OF THE INVENTION

In this invention we have found surprisingly that the anisotropic mechanical property limitations of prior art materials and plates can be eliminated when the flat, plate-like bioabsorbable preform is oriented multiaxially as a consequence of one or more solid state drawing steps with optional solid state compression deformation either before or after the drawing step(s). The solid state compression deformation can be done in a flat, planar mold or in a mold with a 3-dimensional structure, so that plates with a 3-dimensional structure (like groovelike or curved plates) are obtained.

The limitations of prior art materials and plates can be eliminated by making first a non-oriented, flat, plate preform, e.g. a polygon plate, like a triangle, a square or other quadrangle or other polygon or a circular or elliptical plate or a plate with curved edges. Such a preform can be done e.g. with melt molding, like injection molding or extrusion or compression melt molding or with a mechanical, thermomechanical, ultrasound, radiofrequency, laser etc. cutting from a bigger non-oriented plate preform.

According to this invention, multiaxially oriented, broad and long bioabsorbable billets or plates which can be deformed, yet are dimensionally stable, in operation room conditions, can be manufactured from non-oriented plate preforms with the following methods:
- with the solid state multiaxial orientation of the plate preform in one or two or several drawing steps, with optional solid state compression deformation of the plate sample either before or after the drawing step(s).

According to the invention broad and long multiaxially oriented billets or plates can be manufactured (e.g. with the thickness of 0.1-6 mm and with the length up to ca. of 20 cm and with the width of up to ca. 20 cm).

Because of the multiaxial orientation of the polymer material the billets and plates of the invention have a tough, mechanically isotropic structure, so that the billet or plate can be bended and/or twisted in the solid state at room temperature and their structure resists mechanical loads in an isotropic way in different directions, like the splitting (tear) between fixation device holes of the plate (which is made of the plate-like billet).

We have found surprisingly that brittle polymer material, such as bioabsorbable thermoplastic polymers, copolymers, polymer alloys, or composites thereof with optional ceramic particulate fillers or fiber reinforcements, with $T_g$ of the polymer material above body temperature, which materials, as plates, cannot be deformed at room temperature without a risk of breaking them or developing damages, like fractures, cracks or crazes into them, can be transformed into broad and long, strong and tough bioabsorbable plates with solid state multiaxial orientation by drawing and/or by optional compression deformation of the flat, circular, elliptical or polygonal material preforms or plates either before or after the drawing step(s), so that the transformed material preforms or plates are deformable at room temperature and their mechanical properties can be effectively changed by changing the nature and degree of mechanical transformation.

Accordingly, the present invention describes multiaxially oriented, rigid and tough materials and implants, like plates, which plates can be deformed at a first thermochemical state, like at room temperature in operation room conditions, prior to implantation, and which implants retain their deformed (shaped) form so well also in the second thermochemical state, at body temperature, in tissue conditions, when implanted on bone, that they keep the fixed bone fragments essentially in the desired position to facilitate bone fracture healing.

The first thermochemical state can be any temperature below $T_g$ of the material down to the room temperature ($T_{RT}$) area because plates with a multiaxial orientation retain their properties of being substantially deformable and substantially rigid at such temperatures.

Rigid and deformable in this context means that the plate can be bent in a first thermochemical state, especially at room temperature (20-25° C.), to a new configuration which the plate retains owing to its rigidity, until it is again forced to a new configuration which is not necessarily its original configuration. Thus, the plate can be deformed by bending (deformable) several times to a new configuration where it is mechanically stable (rigid) at room temperature.

An advantage of the present invention is to provide a low profile, broad, oriented biocompatible plate implant with a multiaxial orientation structure and with sufficient strength to be operable for enhancing a substantially secured relation between a plurality of adjacent bone portions.

Another advantage of the present invention is to provide a biocompatible plate implant with a multiaxial orientation structure which plate is bioresorbable over a desired period of time while not generating a substantial inflammatory response.

A further advantage of the present invention is to provide a bioabsorbable and biocompatible implant, like plate, with a multiaxial orientation structure, which plate is relatively rigid at a first thermochemical state, but is also relatively deformable at said first thermochemical state prior to implantation.

A further advantage of the present invention is to provide a bioabsorbable plate implant with a multiaxial orientation structure, which plate is repetitively deformable at the said first thermochemical state prior to implantation.

Another advantage of the present invention is to provide a biocompatible plate implant with a multiaxial orientation structure which plate can be easily and inexpensively manufactured with continuous, semi-continuous or non-continuous processes.

Another advantage of the present invention is to provide a biocompatible plate preform with a multiaxial orientation structure which plate preform can be easily and inexpensively manufactured with continuous, semi-continuous or non-continuous processes and cut to smaller plates with mechanical, thermomechanical, ultrasonic, radiofrequency, laser etc. cutting methods, which smaller plates can be cut with an optimal (material saving) way, yet receiving plates with isotropic mechanical properties.

A further advantage of the present invention is to provide a bioabsorbable fixation device with a multiaxial orientation structure, which device is operable to enhance a secured relation between the oriented biocompatible fixation device (plate) and one or more adjacent bone portions.

The present invention, in one embodiment thereof, provides a low-profile oriented biocompatible osteosynthesis plate with a multiaxial orientation structure and operable for being enhanced in a substantially secured relation to a plurality of adjacent bone portions. The osteosynthesis plate includes an elongated or broad section (or sections) having a top face and a bottom face, which section is operable for traversing a fracture site or osteotomy site for subsequent fixation to adjacent bone portions. The oriented osteosynthesis plate further includes a plurality of fastener openings disposed between the top face and bottom face to allow the location of a plurality of surgical fasteners therethrough. The osteosynthesis plate further may include means disposed upon the elongated section to permit the formation of additional fastener openings therethrough during a surgical procedure at the discretion of the surgeon. The osteosynthesis plate is relatively rigid at a first temperature and is deformable in three dimensions, yet dimensionally stable, at said first temperature. The osteosynthesis plate retains a deformed position at said first temperature in operation conditions, but can be subsequently returned to its original configuration by redeformation at said first temperature, at said first thermochemical state. As such, the multiaxially oriented osteosynthesis plate of the present invention may be repeatedly deformed and returned to its original configuration at said first temperature (first thermochemical state) in order to contour the osteosynthesis plate precisely to a desired configuration through successive deformations.

The present invention also includes surgical, bioabsorbable (bioresorbable) fixation devices, like bone screws or tacks, which are operable to be inserted through fastener openings disposed within the multiaxially oriented osteosynthesis plates of the present invention. As such, the present invention contemplates a bone stabilization device including a bioabsorbable osteosynthesis plate with a multiaxial orientation structure and bioresorbable surgical fastener(s).

The present invention also provides methods for forming a low-profile oriented biocompatible, surgical bioabsorbable osteosynthesis plate including the steps of formation of a non-oriented preform, its multiaxial drawing and/or compression deformation to receive an osteosynthesis plate-like billet with multiaxial orientation and optional cutting to smaller plates and finally finishing, surface cleaning, sterilization and packaging of the plate(s).

The present invention also provides a method for enhancing a substantially secured relation between a plurality of adjacent bone portions including the steps of providing a low-profile, biocompatible, osteosynthesis plate with a multiaxial orientation, positioning such a plate upon a plurality of adjacent bone portions, providing a plurality of surgical fasteners for enhancing a fixed relation between the oriented osteosynthesis plate and at least one adjacent bone portion, positioning the plurality of surgical fasteners within a plurality of fastener openings upon the oriented osteosynthesis plate and substantially securing the plurality of surgical fasteners into the adjacent bone portions.

During orientation polymer molecules or their segments tend to align with their long axis in the direction of the orientation. A description of molecular background of orientation of polymeric materials and of its physical characterization is given e.g. in U.S. Pat. No. 4,968,317 and in references therein. The entire disclosure of the U.S. Pat. No. 4,968,317 is incorporated herein by reference. The effects of orientation are most pronounced in partially crystalline polymers, but it is also possible to orient non-crystalline (amorphous) polymers, as has been described in PCT/FI96/00511, the entire disclosure of which is incorporated herein by reference.

BRIEF DESCRIPTION OF THE DRAWINGS

Other advantages of the present invention will become apparent to one skilled in the art upon reading the following specification and the following drawings.

DESCRIPTION OF THE PREFERRED EMBODIMENT

For the purpose of promoting and understanding of the principles of the invention, reference will now be made to the preferred embodiments of the present invention. It will nevertheless be understood that no limitation of the scope of the invention is thereby intended, such alterations and further modifications, and such further applications of the principles of the invention therein being contemplated as would normally occur to one skilled in the art to which the invention relates.

Figure 1:
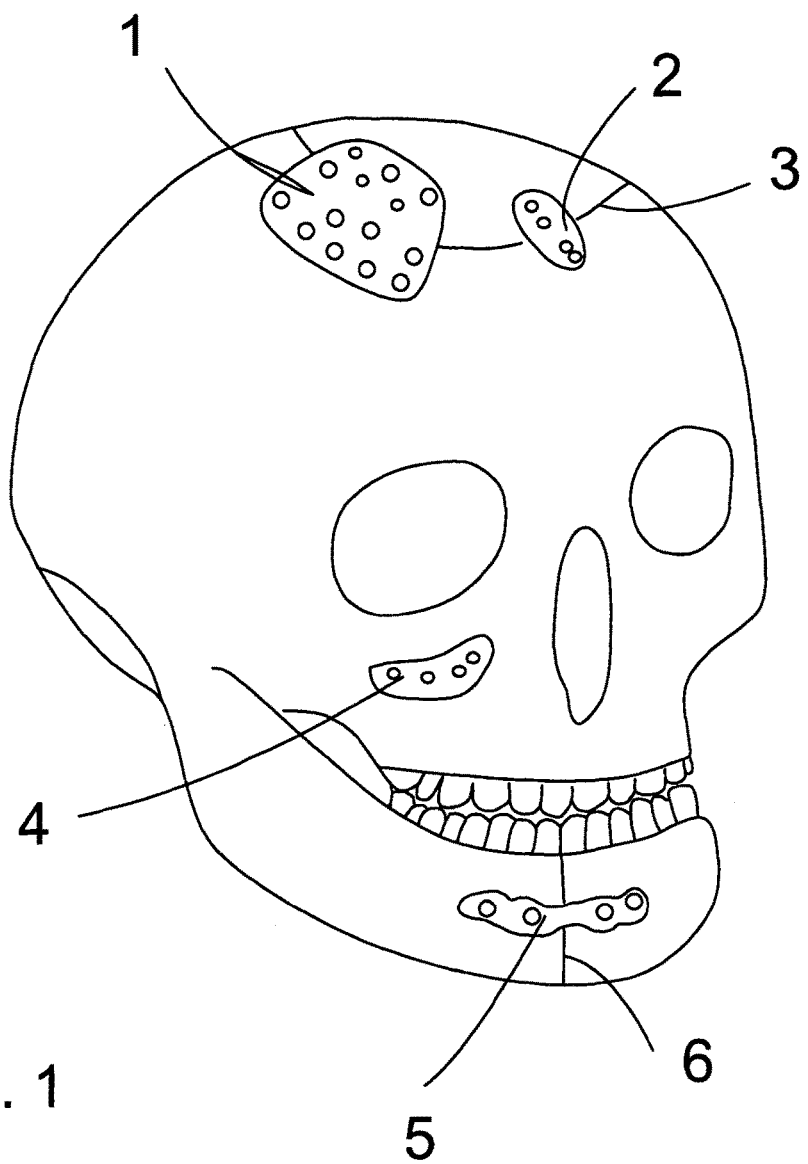
FIG. 1 describes a perspective view of a plurality of multiaxially oriented osteosynthesis plates according the present invention, shown in association with the repair of craniomaxillofacial or mandibular fractures.

Referring to FIG. 1, there is shown a biocompatible, bioabsorbable osteosynthesis mesh plate 1 and elongated plates 2, 4 and 5 with a multiaxial orientation structure according to preferred embodiments of the present invention. The multiaxially oriented biocompatible osteosynthesis plates are shown as being bended and disposed over bone fractures or osteotomies 3 and 6. It will be appreciated that osteosynthesis plates of this invention, like plates 1-2, 4 and 5, may be of any size or shape as will be hereinafter discussed. Further, the osteosynthesis plates, like 1-2, 4 and 5, are deformable and rigid at a first thermochemical state, like in operation room conditions. "A thermochemical state" as used in describing the present invention is defined according to U.S. Pat. No. 5,569,250 as a combination of thermal and chemical conditions resulting from exposure to certain thermal and chemical environments like room temperature and operation room atmosphere, respectively. Although one type of change in thermochemical state occurs by a change of temperature alone, changes in thermochemical state of a multiaxially oriented biocompatible implant of the present invention should be understood as not limited only to changes in temperature.

Preferably, the multiaxially oriented biocompatible, bioabsorbable osteosynthesis plates of this invention are relatively rigid at both room temperature and at human body temperature and they are deformable at temperatures (like at room temperature) below $T_g$ of the material from which the multiaxially oriented biocompatible osteosynthesis plates are made. Therefore there is no need to heat the plates of this invention to temperatures above $T_g$ of the material, as must be done with many prior art plates. Because of the multiaxial orientation of the materials of the invention, they express the substantial rigidity and substantial deformability in all temperatures between $T_g$ of the material and room temperature (in certain cases even at temperatures below room temperature).

Importantly, the multiaxially oriented biocompatible, bioabsorbable osteosynthesis plates of this invention are formed by methods such that they are dimensionally stable and deformable in operation conditions at room temperature and/or at any temperature above room temperature (first thermochemical state) but at or below body temperature (second thermochemical state). As used herein, the term "dimensionally stable" means that the biocompatible, bioabsorbable osteosynthesis plates with a multiaxial orientation are able to retain substantially the same configuration at either of said two thermochemical states so that the multiaxially oriented osteosynthesis plates facilitate bone fracture healing by keeping the fractured pieces in the proper position in relation to each others.

The rigidity, deformability, the dimensional stability and mechanical isotropy in the sheet plane of the plate are due to the manufacturing process of plates with a multiaxial orientation, which is also discussed below. The wide-area opposite surfaces of the plate define a main plane (sheet plane) of the plate where the multiaxial orientation following three or more orientation axes exists. In the plate there are several imaginary planes parallel to the main plane where such a multiaxial orientation exists.

The multiaxially oriented biocompatible osteosynthesis plates, like those of FIG. 1, are typically formed from multiaxially oriented bioabsorbable polymer, copolymer, polymer alloy or composite (with particle filler or fiber reinforcement) preforms. Examples of such materials are e.g. lactide (80-85 mol-%) and glycolide (15-20 mol-%) copolymers which have glass transition temperatures ($T_g$) between 50° C. and 65° C.

Osteosynthesis plates with a multiaxial orientation made using bioabsorbable materials and in the manner discussed below will retain a substantial proportion of their strength after the first several weeks or months after implantation when this strength must be relatively high to facilitate bone fracture or osteotomy healing.

Osteosynthesis plates with a multiaxial orientation may be done of partially crystalline or non-crystalline (amorphous) materials. The multiaxially oriented osteosynthesis plates of this invention are operable to stabilize a plurality of bone portions for a period of from one to several months following implantation and yet be completely resorbed after one year or several years following implantation, depending on such factors as chemical composition and molecular weight of the bioabsorbable polymeric material, implant size and geometry or the position of the implant in a human body. Accordingly, the resorption time can be tailored to be fast or slow. Slow resorption is advantageous in the case of slowly healing fractures and a relatively fast resorption of the bioabsorbable material reduces the unwanted cosmetic appearance as well as growth restriction in pediatric patients.

It will be appreciated that the oriented biocompatible, bioabsorbable osteosynthesis plates of this invention may have a variety of sizes and/or shapes as hereinafter discussed and may also be made of a bioabsorbable polymer material of different origins. In addition, the oriented biocompatible osteosynthesis plates of this invention are preferably both rigid and deformable at room temperature (below $T_g$ of the material) and at human body temperature.

Suitable plate geometries of osteosynthesis plates, which can be applied in manufacturing of the osteosynthesis plates of this invention are given e.g. in prior art, e.g. in U.S. Pat. No. 6,221,075 and in U.S. patent application Ser. No. 09/876,065 and in references therein.

The osteosynthesis plates of this invention are typically flat (with the thickness of 0.1 mm up to 6 mm) and can include one or more fastener openings and/or portions where the surgeon can form additional fastener opening(s) e.g. by drilling. These flat plates can be formed to three-dimensional contour specific for a surgical application also during the manufacturing process to minimize the need of bending the plate during surgical operation.

The flat plates of this invention are provided to be in a "low-profile" construction, that is, of a preferably thin nature so as to cause a minimum protrusion above the bone surface to which they are applied. In this regard, the term "low profile" will be used to refer to a construction in which the width is greater than about four to six times the height of the plate. For example, the mesh-plate may typically have a width and length of 60-100 mm. The elongated plate may typically have a width of 4-8 mm, a length of between about 10 mm to 80 mm (or even up to ca. 200 mm). Typical thickness of plates of the invention can be from ca. 0.1 mm up to 6 mm.

The flat plates of this invention are also characterized by their ability to be deformed, without heating them above $T_g$ of the plate material, during a surgical procedure to be conformed to the contour of the bone surface to which they are applied. This feature is especially useful in the surgical repair of bone surfaces having curvatures, including the maxillofacial and mandibular bones of the craniofacial skeleton, but also bone surfaces in many other parts of human body, like in the extremities, in the thorax and in the spine.

During deformation, the flat plates of this invention are deformed, by manipulating the plate by hands or with special manipulating device(s), in a first thermochemical state, i.e. in operation room conditions during a surgical operation. Accordingly, there is no need to convert the plate before deformation to a higher temperature, using e.g. a heating device, as is needed e.g. in prior art U.S. Pat. No. 5,569,250. The deformed plate of this invention will then be located into the second thermochemical state when fixed on bone to fixate the bone fracture. More preferably, because the flat osteosynthesis plates of this invention are formed by a method which causes the plates to be deformable, ductile, rigid and dimensionally stable during operation in operation room conditions, in the first thermochemical state, the flat plates of this invention are able to return to their original configuration upon deforming them again in operation room conditions. As such, it will be appreciated that this ability allows the flat plates to be repetitively deformed and returned to their original configuration, thus allowing for successive rapid attempts by a surgeon during a surgical procedure to conform the flat plates in three dimensions to correspond as closely as possible to the contours of the bone surface to which the flat plates will be applied. These successive deformations can be done conveniently and rapidly in operation room by operation table without heating and cooling conversions, which are needed in bending of prior art plates, e.g. like those of U.S. Pat. No. 5,569,250.

The formation of additional fastener openings through the flat plates of this invention may be accomplished simply drilling through the material from which the flat plates are made as discussed above. Such drilling is performed through means well known to those skilled in the art. The flat plates are then operable to accept a plurality of surgical fasteners, such as biocompatible and bioabsorbable (bioresorbable) bone screws or tacks, which may be constructed of the same material as the flat plates, or may alternatively be made of another bioabsorbable material.

The positioning of the flat plates of this invention is preferred to be with their bottom face in substantially flush contact with the bone surface to which they are applied, and with a plurality of fasteners disposed therethrough to an enhanced secured position, wherein the head of the surgical fastener is tightened against the top face of the flat plate of this invention. This arrangement results in an enhanced secured relation between the flat plate of this invention and the underlying bone surface. According to an advantageous embodiment the fastener opening is conically widened from its opening end on the top face of the plate so that it forms a countersink on the top face of the plate to match with the head of the fastener.

In addition to a simple plate with a constant width and one or several fastener openings the multiaxially oriented, bioabsorbable plates of the invention can have such a design that the width of the plate in the area of the isthmus between two fastener openings is smaller than the width of plate around the fastener openings (or the width of the area into which additional fastening openings can be drilled). Such a plate can be seen e.g. in FIG. 1, the plate 5. A special advantage of such plates is that these plates can be deformed easily also in the flat plane of the plate in addition to bending and torsional deformations, which are typical for constant width plates. Also the thickness of flat plates of this invention can be different in different parts of the plate. E.g. low profile stiffening ridges can be constructed on the surface of the plate.

When fully inserted, the head of the bone fixation screw or other fastener may be mainly or substantially contained at or below the top face of the plate of the invention, thereby complementing the low-profile configuration of the osteosynthesis plate. The bone screw or other fastener may be made from the same or different biocompatible and bioabsorbable material as the osteosynthesis plate, thereby providing a fully bioresorbable bone stabilization device system.

Referring to prior art, like U.S. Pat. No. 6,221,075, there are available a plurality of geometries or configurations of osteosynthesis plates which configurations can be applied in manufacturing of multiaxially oriented plates of the present invention. Typical configurations of such plates are e.g. I-plates (straight plates), L-plates, T-plates, Y-plates, X-plates, H-plates, mesh-plates like circular or elliptical plates, square-plates and triangle plates, etc.

Flat plates of this invention can also be bended during manufacturing in the flat plane of the plate and/or in any other plane to achieve any desired 2- or 3-dimensional geometry of the plate. The plane of the plate shall in this context be interpreted as a plane that may be flat or curved, following the shape of the surfaces of the plate whose mutual distance determines the thickness of the plate.

The lower surface of the plate, which is in contact with the bone, can include protuberances and/or ridges to keep a part of the plate above the bone surface to reduce the compression of the plate to the bone surface.

All the plates of this invention may include a plurality of holes for fasteners, depending on the size and use indications of the plate.

According to an advantageous embodiment of this invention the plates can be mesh-plates with a plurality of smaller holes for fastener fixation and optional smaller or bigger or equal-size holes to facilitate tissue healing through the plate and to reduce the mass of the plate.

It will be appreciated that the examples set forth above are meant to be illustrative of the varieties of osteosynthesis plate shapes which may be constructed according to the present invention. It will further be appreciated that these osteosynthesis plates may be constructed of any of the materials previously discussed, or may be constructed from other suitable bioabsorbable materials. As before, it is preferred that any of the above osteosynthesis plates be constructed of a bioabsorbable (bioresorbable) material. As before, the bioabsorbable material may be combined in a bone stabilization device with bioabsorbable surgical fasteners, such as bone screws and/or tacks.

In addition, it will be appreciated that any of the above osteosynthesis plates may be constructed to include means disposed upon the elongated section to permit the formation of additional fastener openings therethrough during a surgical procedure, as provided e.g. in EP 0 449 867 B1. Further, all of the above-mentioned osteosynthesis plates are intended to be of a low-profile configuration, constructed preferably in a flat configuration.

The osteosynthesis plates of the present invention can be manufactured of thermoplastic bioabsorbable (bioresorbable or biodegradable) polymers, copolymers, polymer alloys, or composites e.g. of poly-α-hydroxy acids and other aliphatic bioabsorbable polyesters, polyanhydrides, polyorthoesters, polyorganophosphatzenes, tyrosine polycarbonates and other bioabsorbable polymers disclosed in numerous publications, e.g. in S. Vainionpää et al., Prog. Polym. Sci., 14 (1989) 679-716, FI Pat. No. 952884, FI Pat. No. 955547 and WO-90/04982, EP 0449867 B1, U.S. Pat. No. 5,569,250, S. I. Ertel et al., J. Biomed. Mater. Res., 29 (1995) 1337-1348 as well as in the reference publications mentioned in the aforementioned publications.

Implants in accordance with this invention can be manufactured of bioabsorbable polymers by using one polymer or a polymer alloy. The implants can also be reinforced by reinforcing the material by fibres manufactured of a resorbable polymer or of a polymer alloy, or with biodegradable ceramic fibres, such as β-tricalsiumphosphate fibres, bioactive glass fibres or CaM fibres (cf. e.g. EP146398). Ceramic powders can also be used as additives (fillers) in implants to promote new bone formation.

Implants according to the invention can also contain layered parts comprising e.g. (a) a flexible outer layer as a surface layer improving the toughness and/or operating as the hydrolysis barrier and (b) a stiff inner layer.

It is natural that the materials and implants of the invention can also contain various biocompatible additives for facilitating the processability of the material (e.g. stabilizers, antioxidants or plasticizers) or for changing its properties (e.g. plasticizers or ceramic powder materials or biostable fibres, such as carbon) or for facilitating its treatment (e.g. colorants).

According to one advantageous embodiment the implant of the invention contains some other bioactive additive(s), such as antibiotic(s) and/or other drug(s), chemotherapeutic agents, agents activating healing of wounds, growth factor(s), bone morphogenic protein(s), anticoagulant (such as heparin), hemostatic agents, etc. Such bioactive implants are particularly advantageous in clinical use, because they have, in addition to their mechanical effect, also biochemical, medical and other effects to facilitate tissue healing and/or regeneration.

A typical manufacturing procedure to make plates of the present invention is as follows:

First the polymer raw material (+optional additives and/or filler(s) and/or reinforcing fibers) in the form of a powder, flakes, pellets or granulate, etc., will be melted (melt molded) with a continuous process, like extrusion, or with a non-continuous process, like injection molding or compression molding. The melted material will be cooled so that it solidifies to an amorphous or partially crystalline (crystallinity typically 5-70%) plate preform. Cooling can be done inside a special mold in injection molding and in compression molding techniques. In extrusion, the preform will be formed from material melt in a die and the preform will be led onto a special cooling belt or into a cooling solution to make a solid continuous plate preform. The injection molded or compression molded preform can be circular, elliptical or another plate with curved edges or polygonal, like triangular or quadrangular. The desired preform can be formed also by cutting the melt molded preform with a suitable cutting method, like with mechanical or thermomechanical or ultrasonic or laser, etc. method. Thereafter the proper plate preform is oriented at a temperature above $T_g$ of the material, but below $T_m$ (if any) of the material. According to the invention, the orientation is done multiaxially, by drawing the plate preform at least in the direction of three different axes. The multiaxial orientation can be done either in one orientation step or in two or several steps.

Figure 2A:
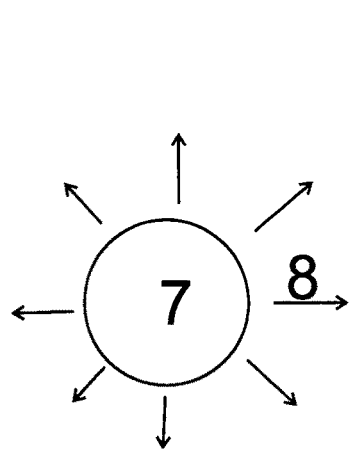
FIGS. 2A-B show schematically the multiaxial solid state drawing of a circular, flat, non-oriented plate preform in a single drawing step to a multiaxially oriented plate.
Figure 2B:
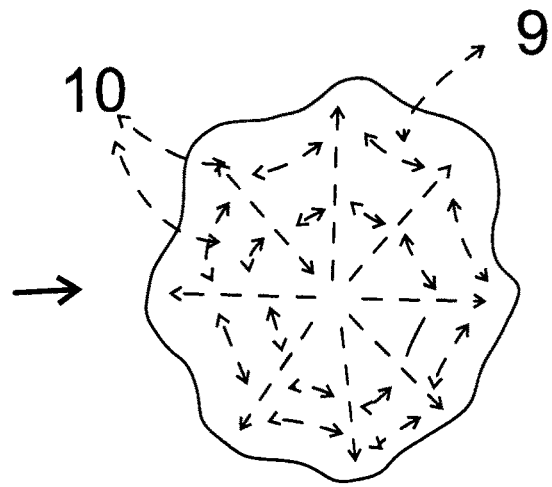

In FIG. 2A is shown schematically how the circular, nonoriented plate preform 7 is drawn multiaxially into the direction of four orientation axes. One of the axes is described with number 8. This kind of multiaxial orientation can be done in practice e.g. by gripping the drawing heads to the edges of the preform and by drawing the drawing heads in the plane of the flat surfaces of the preform to the radial directions as described in FIG. 2A. FIG. 2B shows schematically the multiaxially drawn plate 9 with the draw ratio of ca. 2 (The draw ratio is the final certain dimension of the plate divided by the original corresponding dimension, like the radius of the circular plate. The necessary draw-ratio depends on several factors, like on the polymer structure the drawing temperature, the drawing speed and the structure of the preform. The draw ratios from 1.5 up to 3.5 are typically used although higher draw ratio also can be used in some cases). During the multiaxial drawing solid state flow and orientation of the material occurs both in the radial and tangential directions and in directions between them. Some typical orientation directions are described in FIG. 2B with broken line arrows 10. Because of multiaxial orientation, the plates of the invention have more uniform mechanical properties in different directions than the prior art mono- and biaxially oriented plates have. Therefore oriented perform plate, like 9, can be cut effectively in desired, different directions to smaller elongated or mesh plates, with isotropic (uniform) mechanical properties in different directions. A similar one-step drawing process to obtain a multiaxially oriented plate can be applied to an elliptical preform as well. As a result of the method of FIG. 2A, the polymer material of the plate will be arranged according to four orientation axes that are spaced at equal angular distances over a full circle, that is, at distances of 45°.

Figure 3A:
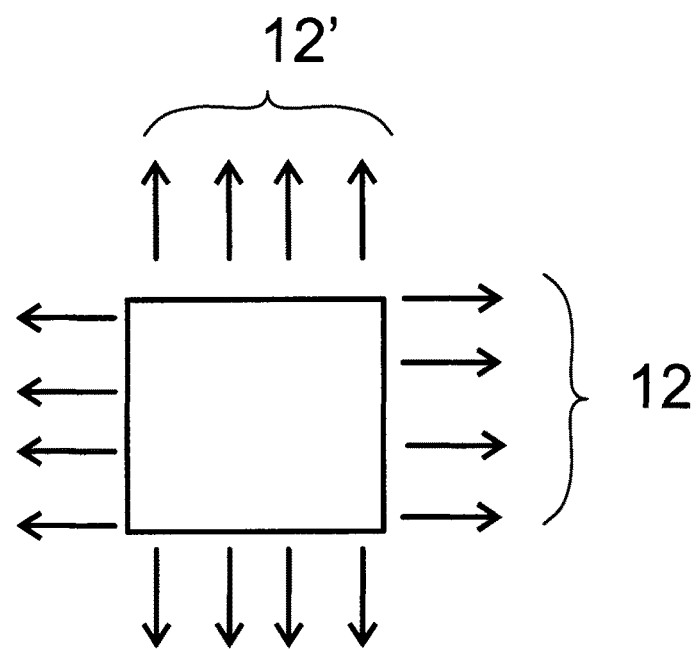
FIGS. 3A-3D show schematically the two drawing steps, process of drawing a quadrangular (square), non-oriented plate preform to a multiaxially oriented plate.
Figure 3B:
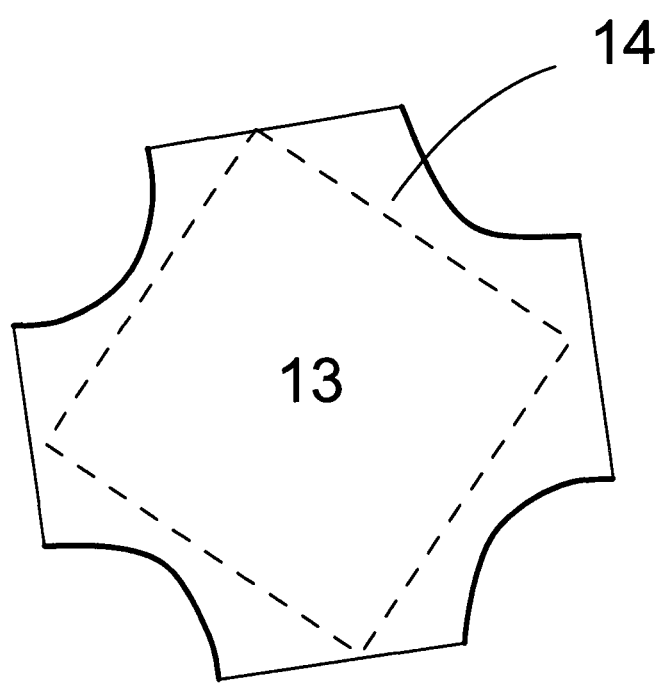
Figure 3C:
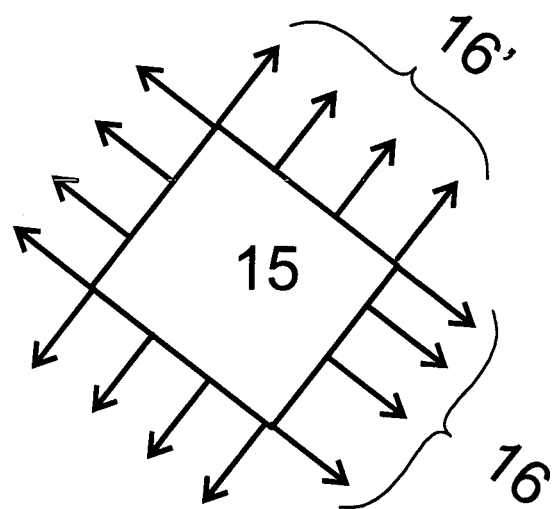
Figure 3D:
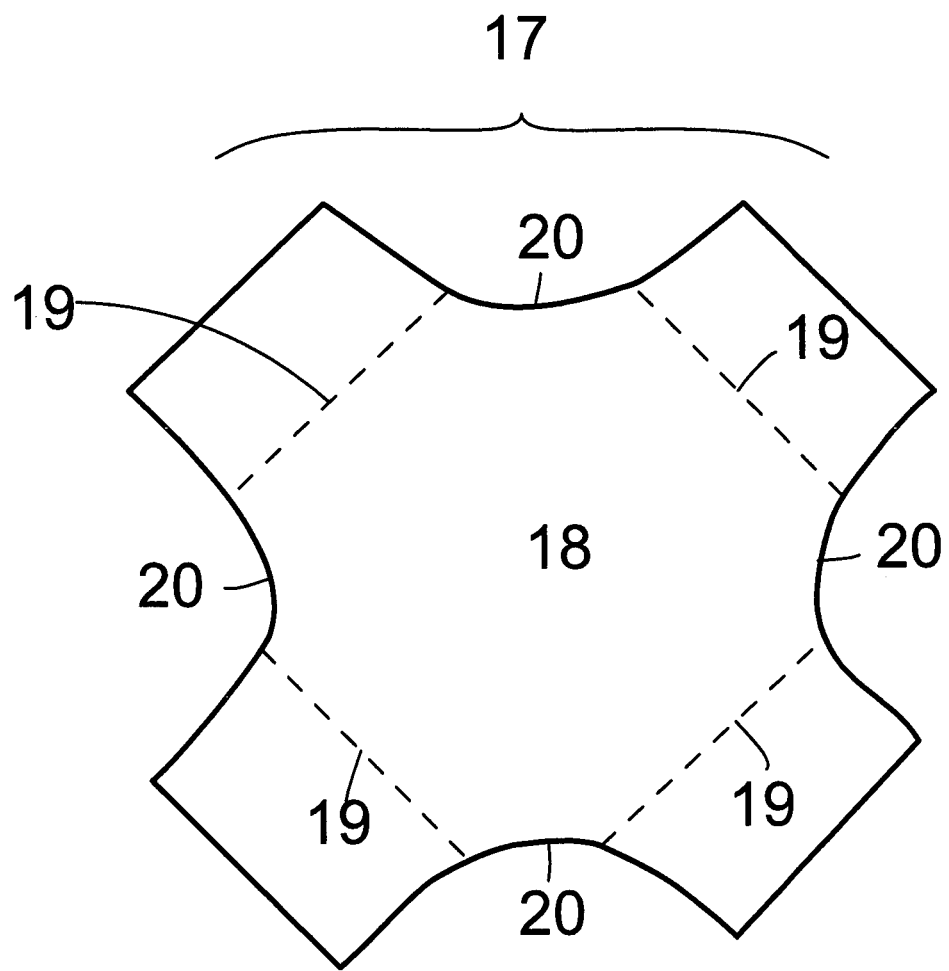

FIGS. 3A-D show schematically the two orientation steps process to make a multiaxially oriented plate. FIG. 3A shows a quadratic plate perform 11, which is drawn simultaneously into two directions 12 and 12' along two orientation axes, which are perpendicular to each other. The draw ratio is ca. 2. The drawn plate 13 is seen in FIG. 3B. The plate 13 is then cut along the dotted line 14 to a new quadratic plate 15 so that its diagonals will coincide approximately with the orientation axes of the first drawing step, seen in FIG. 3C. The plate 15 is now drawn in two perpendicular directions 16 and 16' along two orientation axes that are angularly displaced with respect to the orientation axes of the first drawing step and angularly midway between them, giving the final plate 17, which has the strongly multiaxially oriented core area 18 (which is marked in FIG. 3D with broken lines 19 and curved edges 20 between the broken lines 19).

Figure 4A:
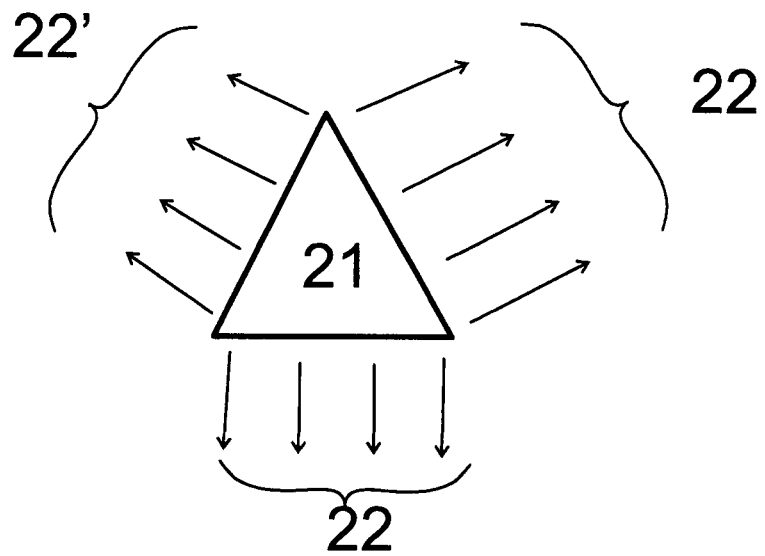
FIGS. 4A-B show schematically the multiaxial (triaxial) drawing of a triangular, non-oriented plate preform to a multiaxially oriented plate in a single drawing step.
Figure 4B:
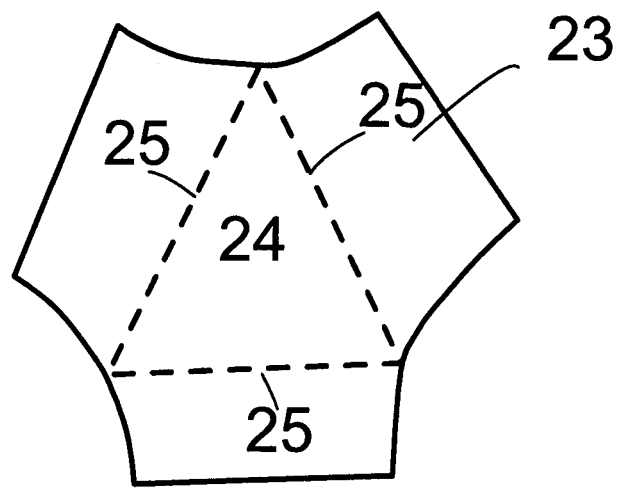

FIG. 4A shows schematically, how an equilateral, triangular, non-oriented plate preform 21 is drawn simultaneously in three different directions 22, 22' and 22", along three orientation axes spaced from each other at equal angular distances over a full circle (360°), with the draw ratio of ca. 2, yielding the plate 23, which has the strongly multiaxially oriented core area 24, which is marked with broken lines 25.

It could be possible to increase the number of orientation axes in the multiaxially oriented plate above three, to six, by cutting a new triangle with center line of each angle coinciding approximately with the original orientation axis and performing the drawing step along three orientation axes running along angular positions midway between the original orientation axes (axes of the first step) and approximately perpendicularly to the sides of the new triangle that were formed by cutting. After the second drawing step the strongly multiaxially oriented core area can again be separated from the drawn plate. This principle of two successive drawing steps where the orientation axes of the second step are midway between the orientation axes of the first step can be applied in analogous manner to all preforms that have the initial shape of a polygon so that the final number of the orientation axes will be two times the number of sides of the polygon.

According to an advantageous embodiment of this invention the non-oriented plate preform is compressed (deformed) to a thinner plate at a temperature above $T_g$, but below $T_m$, of the material, before the drawing step(s). When e.g. a circular plate preform (the thickness e.g. from 4 mm up to 15 mm and radius from 4 cm up to 15 cm) is compressed to a flatter, circular plate, with two times bigger radius than before the compression, a multiaxial orientation state, comprising both radial and tangential orientations, is achieved. This multiaxial orientation state of the plate can then be developed further with one or more drawing steps. The compression can be combined with rotational movement where the press surfaces flattening the plate perform relative rotational movement around an axis perpendicular to the main plane of the plate simultaneously with the pressing movement.

The orientation drawing can be combined with the rolling of the non-oriented or partially oriented preform between rollers, which flatten the non-oriented or partially oriented preform to the desired plate thickness, when the preform is drawn through the rollers, using e.g. the roller construction whose principle has been described in U.S. Pat. No. 6,221,075, in its FIGS. 10 A and B. The entire disclosure of the U.S. Pat. No. 6,221,075 is incorporated herein by reference. After one drawing through the rollers, the billet is turned to a notable angle (e.g. like to 45 degrees) in relation to the original drawing direction, and the billet is drawn again through the rollers, which flatten it further to the final thickness. The second rolling creates also the multiaxial orientation into the billet. The process can be continued to the third, fourth etc. roller treatment, if desired.

The preform and/or compression plates or die, or rolls can be heated to the desired deformation temperature with electrical heating, with infrared radiation or with a suitable heating medium, like gas or heating liquid. The heating can be done also with microwaves or ultrasonically to accelerate the heating of the preform.

Multiaxially oriented plates (plate preforms), which are obtained by the methods of the invention can be processed to different surgical osteosynthesis plates, like to meshplates, by cutting them to suitable lengths and widths and by making suitable perforations to them. Other plates, like I-, Y-, X-, L-, etc. plates, can be made of drawn plates with suitable mechanical machining or with other cutting methods.

Solid state deformation, to create oriented bioabsorbable fixation materials, has been described in several publications, like in U.S. Pat. No. 4,671,280, U.S. Pat. No. 4,968, 317, U.S. Pat. No. 4,898,186, EP 0 321176 B1 and WO 97/11725, D. C. Tunc and B. Jadhav, in Progress in Biomedical Polymers, eds. C. G. Gebelein and R. L. Dunn, Plenum Press, New York 1992, p. 239-248, FI Pat. No 88111, FI Pat. No 98136 and U.S. Pat. No. 6,221,075. However, only in this invention we have found surprisingly, that when the rigid bioabsorbable (bioresorbable) fixation implant material, which cannot be deformed substantially without damage at temperatures below $T_g$ of the material, is oriented multiaxially, it is also changed to a material which is substantially rigid and mechanically isotropic in the sheet plane of the plate and can be deformed substantially at temperatures below $T_g$ of the material to use it advantageously in bone fracture fixation.

The multiaxial orientation gives for the plate-like billet excellent ductility and toughness so that it can be deformed at room temperature without breaking.

According to an advantageous embodiment of the invention the multiaxially oriented preform plate or the final, cut plate can be covered with a tube-like fibrous fabric ("stocking"). This can be a tube-like braid, textile, etc. which is slipped on to the preform plate or final plate. Thereafter the stocking is fixed on the surface of the preform plate or final plate by means of heat and pressure. The tube-like fibrous fabric can be knitted, weaved, twisted or manufactured of bioabsorbable polymeric and/or biodegradable ceramic or bioactive glass fibers by some other textile technology method. By selecting the fibers of the fabric in a proper way, it is not damaged during compression, but forms a tight reinforcing and stiffening structure on the surface of the multiaxially oriented plate.

The next step of the method of the present invention may involve the finishing of the plates, to enhance smooth surfaces and an aesthetic appearance of the article. This could be accomplished by trimming with suitable trimming devices, such as knives or cutting blades, or may also be accomplished by an additional stamping step. Once the removal of surface irregularities has occurred, the substantially completed product may be subjected to cleaning with a suitable cleaning agent, like ethyl alcohol water mixture. Mechanical agitation and ultrasonic agitation can be used to facilitate the cleaning. In this step, the outer surfaces of the osteosynthesis plate can be cleaned of fingerprints, soils and oils resulting from contact with human hands and other surfaces, as well as impurities which may collect on the surface.

In the next step of the method of the present invention the plates are dried in a high vacuum, optionally at an elevated temperature, packed into a plastic foil and/or aluminium foil pouch(es) which is (are) sealed. Another drying step and filling of the pouch with an inert gas (like nitrogen or argon gas) before heat sealing of the pouch, may also be carried out.

Finally the plates closed into the packages, are sterilized, e.g. with γ-radiation, using a standard dose of radiation (e.g. 2.5-3.5 MRad). If gas sterilization will be used (like ethylene oxide), the plates must be sterilized before closing the package.

It is natural that the above-mentioned steps of manufacturing an osteosynthesis plate of the present invention may further include additional steps, such as for quality control purposes. These additional steps may include quality control testing during or between the various steps, as well as final product inspection including chemical and/or physical testing and characterization steps and other quality control testing.

The method for enhancing a substantially secured relation between a plurality of adjacent bone portions according to the present invention is described next. The first step of this method includes providing a sterile, low-profile, multiaxially oriented biocompatible osteosynthesis plate of the invention. This is achieved by opening the plate package in an operation room by an operation table and supplying the sterile plate to the surgeon. Depending on the surface topography of the bone to be fixed the surgeon then shapes (deforms), if necessary, the osteosynthesis plate to a first desired configuration by hands or with special manipulation instrument(s). The surgeon can then test the result of shaping conveniently by pressing the plate gently against the bone to be fixed and if the first desired configuration is not sufficient for completing the surgical requirements, the surgeon can reshape the osteosynthesis plate to a second desired configuration.

In addition, it will be appreciated that the method of the present invention further includes the capability for repetitively reshaping, at constant operation room temperature, the osteosynthesis plate to successive desired configurations and ceasing reshaping the osteosynthesis plate when a desired final configuration of the osteosynthesis plate has been achieved.

The osteosynthesis plate is then positioned upon a plurality of adjacent bone portions. A plurality of surgical screws or other fasteners are then provided for enhancing a fixed relation between the osteosynthesis plate and at least one adjacent bone portion. A plurality of surgical screws or other fasteners are then positioned within a plurality of fastener openings located upon the osteosynthesis plate. The plurality of surgical screws or other fasteners are then secured to the adjacent bone portions, thereby engaging the low-profile biocompatible osteosynthesis plate with each bone portion. Because the plate has the isotropic mechanical properties in the sheet plane of the plate, the fastener openings can be located quite freely upon the plate.

This method may further include the additional steps of creating at least one additional fastener opening through the osteosynthesis plate at a location adjacent to at least one bone portion, positioning an additional surgical fastener (like a screw or other fastener) within each additional fastener opening, and substantially securing each additional surgical fastener into each bone portion thereby enhancing an engagement of the osteosynthesis plate with each bone portion as was described e.g. in EP 0 449 867 B1. This method may also include the step of engaging the osteosynthesis plate with at least one adjacent osteosynthesis plate.

Alternatively, the method for enhancing a substantially secure relationship between a plurality of adjacent bone portions is similar to that described above, but the osteosynthesis plate is secured by means of an adhesive. In this regard, after the osteosynthesis plate is formed in the manner described above, the surgeon places an adhesive between the bone portions to be secured and the osteosynthesis plate. The surgeon then brings the osteosynthesis plate into contact with the bone portions thereby securing the osteosynthesis plate to the bone portions.

The principles of the present invention described broadly above will now be described with reference to the following specific examples, without intending to restrict the scope of the present invention.

EXAMPLE 1

Manufacturing of Multiaxially Oriented Plate Samples in a Two Step Orientation Process Commercially available medical grade PLGA 85L/15G polymer granulate (Boehringer Ingelheim, Ingelheim, Germany, Resomer LG855S) was compression molded at 220° C. to form a 85×85 mm 4 mm thick plate. This plate preform was biaxially oriented at 80° C. (in two, right angled directions, as in FIG. 3a) to the draw ratio of 1.7 in each directions. Sample was subsequently cooled down to the room temperature under tension. A new preform having the equal size with the preform plate (85×85 mm), but thinner, was cut out of this preform in 45° angle to orientation directions (as in FIG. 3B). This new preform was again oriented biaxially but at 90° C. to the draw ratios 1.7 AND 1.7 in directions plus/minus 45 degrees compared with the orientation directions of the first orientation step (as in FIG. 3 C). The sample was subsequently cooled down to room temperature under tension in the free air and released from the orientation machine.

Manufacturing of a Biaxially Oriented Plate Sample

Biaxially oriented plate material was made out of a similar compression molded preform, as above, with biaxial orientation using simultaneous stretching in two axis to draw ratio of 3 at 85° C. temperature. The sample was allowed to cool down to room temperature under tension in the free air before releasing it from the orientation machine.

Tear Testing

Figure 5:
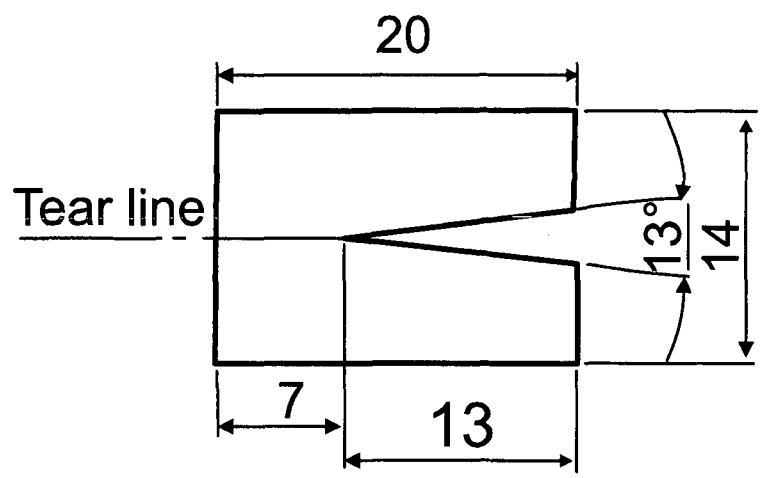
FIG. 5 shows a tear test sample plate, as shown from above, with dimension given in millimeters.

Three samples, one in primary orientation direction (the first orientation axis of the biaxial orientation method), second in secondary orientation direction (the second orientation axis of the biaxial orientation method) and third in 45° angle between these two main axes, were cut out of the both plate materials with a laser cutter for tear testing. The form and dimensions of samples in millimeters, are given in FIG. 5 (as seen from above). The samples were cut out of the plate materials in the three different angles, as described above, in relation to the orientation directions by placing the tear line along the desired test direction. Samples were torn apart along the tear line using a universal material testing machine (MTS Insight 30, MTS Systems inc., Eden Prairie, USA) at the speed of 10 mm/min. Maximum load needed to tear the sample apart was recorded. The results are reported as the load value (N) divided by the thickness of the sample (mm) in order to even out the differences caused by the thickness variations of the samples. For the multiaxially oriented plate the test yielded tear load carrying capacities 32, 30 and 27 N/mm in the primary orientation direction, in the 45° angle to main orientation directions and in the secondary orientation direction, respectively. The test results of similar test for biaxially oriented material yielded 35, 53 and 38 N/mm, in respective directions. It can thus be concluded that the multiaxial orientation method yields practically homogeneous (isotropic) mechanical properties in different directions of the plane, whereas tear properties in biaxially oriented sheet material are nonhomogeneous (anisotropic) in different directions of the plane.

The isotropic mechanical structure is advantageous for the oriented plate perform, especially when smaller plates with complex structure are planned and manufactured of big plate performs, while the big plate preform can be used in an optimal way to produce as many plates with isotropic mechanical properties as possible.

The multiaxially oriented material can further be processed e.g. by compression molding or die drawing process to create desired surface topography and surface quality. The final product, namely the surgical plate, can be cut out of this preform with a laser. The plate can be dried in a vacuum and packed into an aluminum foil pouch in a plate holder to facilitate aseptic handling in operating room. Protective gas ($N_2$) can be applied in the packaging process to reduce the humidity in the packaging and thus TO increase the shelf life of the product. Packed final product can be sterilized using a standard gamma sterilization method with 25 kGy radiation dose.

EXAMPLE 2

Manufacturing of Multiaxially Oriented Plate Samples in a Single Step Orientation Process Commercially available medical grade PLGA 85L/15G polymer granulate (Boehringer Ingelheim, Ingelheim, Germany, Resomer LG855S) can be compression molded at 220° C. to form a 100 mm diameter 4 mm thick round plate. This plate preform can be multiaxially oriented at 85° C. by drawing it e.g. in a self-made orientation machine, with the principles as described in FIGS. 2A-2B, using e.g. 10 separate grippers along 5 different evenly distributed axes of orientation (36° angle between the axes) to the diameter of 300 mm to achieve overall multiaxial draw ratio of 3. Sample can subsequently be cooled down to room temperature in the free air under tension and can be released then from the multiaxial orientation machine.

Tear Testing

Three tear test samples (according to FIG. 5) tear lines in 45° angle between the samples, (the first sample with the tear line in the horizontal radius direction of FIG. 2 B, the second sample with the tear line 45° obliquely upwards from the horizontal direction and the third sample with the tear line 90° upwards from the horizontal direction) can be cut out of the plate material with a laser cutter. Samples can be torn apart along the tear line using a universal material testing machine (e.g. MTS Insight 30, MTS Systems inc., Eden Prairie, USA) at the speed of 10 mm/min. Maximum load needed to tear the samples apart will be recorded. The results can be reported as the load value (N) divided by the thickness of the sample (mm) in order to even out the differences caused by the thickness. The tests yield values ca. 50 N/mm in all the measured directions. So it can be concluded that the multiaxial orientation method yields homogeneous (isotropic) mechanical properties in different directions of the sheet plane of the oriented plate preform.

As a summary, the multiaxial osteosynthesis plate which can have any of the constructions mentioned above, or as defined in any of the attached claims, can be used in a method for securing a plurality of bone portions, said method comprising the steps of:

forming said osteosynthesis plate, said step of forming said plate including:

(a) providing a material that is substantially rigid and substantially deformable and dimensionally stable at a first thermochemical state;

(b) forming said material into said osteosynthesis plate; and (c) securing said osteosynthesis plate to the plurality of bone portions.

Preferably, said method comprises the steps of:

providing an osteosynthesis plate with a multiaxial orientation, said osteosynthesis plate, being operable to be placed in a substantially secured relation with respect to the plurality of bone portions, said plate being composed of a material that is substantially rigid and dimensionally stable and substantially deformable at a first thermochemical state, said osteosynthesis plate including a planar section having first and second surfaces;

deforming said osteosynthesis plate at said first thermochemical state;

securing said osteosynthesis plate to the plurality of bone portions; and leaving the said osteosynthesis plate secured to the plurality of bone portions to allow absorption after fracture healing.

The method for securing a plurality of bone portions can comprise the additional step of forming at least one opening between said first and second surfaces of said osteosynthesis plate after formation of said plate.

According to an advantageous embodiment of the method for securing a plurality of bone portions, said osteosynthesis plate is formed in a first configuration, and said step of deforming said osteosynthesis plate comprises the changing of the shape of said osteosynthesis plate from said first configuration to a second configuration when said osteosynthesis plate is in a first thermochemical state.

Further, in the method for securing a plurality of bone portions said step of deforming said osteosynthesis plate comprises preferably the steps of:

(a) changing the shape of said osteosynthesis plate while at said first thermochemical state; and (b) repeating step (a) until a desired configuration of said osteosynthesis plate has been obtained.

According to an advantageous embodiment, the method for securing a plurality of bone portions comprises the steps of:

providing an osteosynthesis plate with a multiaxial orientation, said osteosynthesis plate being operable to be placed in a substantially secured relation with respect to the plurality of bone portions, said osteosynthesis plate including a planar section having first and second surfaces, said osteosynthesis plate being formed from a material that is substantially rigid and substantially deformable and dimensionally stable when at said first thermochemical state;

forming at least one opening between said first and second surfaces of said osteosynthesis plate;

securing said osteosynthesis plate to the plurality of bone portions; and leaving said osteosynthesis plate secured to the plurality of bone portions to allow bioabsorption after the plurality of bone portions have consolidated (ossified) together.

In any of the above embodiments of the method for securing a plurality of bone portions, said material that is substantially rigid and substantially deformable and dimensionally stable at a first thermochemical state is deformable along three mutually perpendicular axes.

The invention claimed is:

1. A bioabsorbable surgical osteosynthesis plate, operable to be secured by at least one fastener through at least one fastener opening formed in the plate to a bone, said osteosynthesis plate comprising:
a flat section having first and second surfaces defining a main plane of the plate which is a sheet plane of the plate, the plate comprising a polymer material, including at least one of a polymer, copolymer or polymer alloy, said polymer material being oriented multiaxially to form an multiaxially oriented structure of the plate and being substantially rigid and substantially deformable at a first thermochemical state, and being arranged in the multiaxially oriented structure of the plate according to three different orientation axes along the main plane of the plate as a result of solid state drawing of the plate, the polymer material of the plate having isotropic mechanical tear properties in different directions along the main plane of the plate and said plate having isotropic resistance against splitting and internal delamination.

2. The surgical osteosynthesis plate according to claim 1, wherein the polymer material is arranged according to at least four different orientation axes.

3. The surgical osteosynthesis plate according to claim 2, wherein the orientation axes are spaced at regular angular distances in the main plane of the plate.

4. The surgical osteosynthesis plate according to claim 1, wherein the orientation axes are spaced at regular angular distances in the main plant of the plate.

5. The surgical osteosynthesis plate according to claim 1, wherein said osteosynthesis plate is at a first configuration at a first thermochemical state and is operable to be deformed to a second configuration at said first thermochemical state.

6. The surgical osteosynthesis plate according to claim 5, wherein said biocompatible osteosynthesis plate is operable to substantially retain said second configuration in conditions of a surgical operation in said first thermochemical state.

7. The surgical osteosynthesis plate according to claim 6, wherein said osteosynthesis plate is operable to substantially change from said second configuration to said first configuration at said first thermochemical state.

8. The surgical osteosynthesis plate according to claim 7, wherein said biocompatible osteosynthesis plate is operable to be repetitively deformed to different configurations at said first thermochemical state.

9. The surgical osteosynthesis plate according to claim 1, wherein said polymer material has a glass transition temperature, and wherein said osteosynthesis plate is initially formed at a first thermochemical state to have a first configuration, said osteosynthesis plate being formed from a material that is dimensionally stable in said first configuration at body temperature just after fixation on a bone surface in a surgical operation.

10. The surgical osteosynthesis plate according to claim 1, wherein said polymer material comprises a bioabsorbable polymer, copolymer or polymer alloy, or a mixture of a bioabsorbable polymer, copolymer or polymer alloy and bioceramic or bioactive glass particles or fibers.

11. The surgical osteosynthesis plate according to claim 1, wherein the plate is covered with a fibrous fabric surrounding the plate.

12. An implantable bioabsorbable bone stabilization device for stabilizing a plurality of bone portions, said device comprising:
a biocompatible osteosynthesis plate comprising a flat section having first and second surfaces defining a main plane of the plate which is a sheet plane of the plate, the plate comprising a polymer material, including at least one of a polymer, copolymer or polymer alloys, said polymer material being oriented multiaxially to form a multiaxially oriented structure of the plate an being substantially rigid and substantially deformable at a first thermochemical state, and being arranged in the multiaxially oriented structure of the plate according to at least three different orientation axes along the main plane of the plate as a result of solid state drawing of the plate, the polymer material of the plate having isotropic mechanical tear properties in different directions along the main plane of the plate, said plate having isotropic resistance against splitting and internal delamination; and
an attachment structure configured to attach said plate to a plurality of bone portions.

* * * * *